United States Patent [19]

Hoshiyama et al.

[11] 4,447,661
[45] May 8, 1984

[54] PROCESS FOR PRODUCING AN ALCOHOL BY HYDROFORMYLATION

[75] Inventors: Satoshi Hoshiyama; Hiroyuki Muto; Shuzo Shinke; Kanji Otsuka; Shinichiro Takigawa; Hiroyuki Yamazaki, all of Funabashi, Japan

[73] Assignee: Nissan Chemical Industries Ltd., Tokyo, Japan

[21] Appl. No.: 415,236

[22] Filed: Sep. 7, 1982

[30] Foreign Application Priority Data

Sep. 7, 1981 [JP] Japan ............................. 56-140664

[51] Int. Cl.³ .......................................... C07C 45/50
[52] U.S. Cl. .................................. 568/882; 568/454; 568/884; 568/909
[58] Field of Search ............... 568/451, 454, 909, 882, 568/884

[56] References Cited

U.S. PATENT DOCUMENTS

| | | | |
|---|---|---|---|
| 3,127,451 | 3/1964 | Berleley et al. | 568/451 |
| 3,448,157 | 6/1969 | Slaugh et al. | 568/454 |
| 3,448,158 | 6/1969 | Slaugh et al. | 568/454 |
| 3,896,047 | 7/1975 | Aycock et al. | 568/454 |
| 4,183,871 | 1/1980 | Tavs et al. | 568/909 |
| 4,320,237 | 3/1982 | Koufhold et al. | 568/909 |
| 4,322,564 | 3/1982 | Tsundda et al. | 568/909 |

*Primary Examiner*—Werren B. Lone

*Attorney, Agent, or Firm*—Oblon, Fisher, Spivak, McClelland & Maier

[57] ABSTRACT

In a process for producing an alcohol by hydroformylation comprises reacting a straight chained, branched or alicyclic mono-olefin having from 3 to 20 carbon atoms with carbon monoxide and hydrogen to form an alcohol having carbon atoms greater in number by one than the carbon atoms of the mono-olefin, the improvement comprises (a) a fist step in which the mono-olefin is hydroformylated with use of a cobalt catalyst in the presence of a gas mixture of carbon monoxide and hydrogen at a high temperature under high pressure to selectively form an aldehyde at a conversion of the mono-olefin being from 50 to 95 mol % while suppressing the formation of an alcohol, and the cobalt catalyst is then removed from the unreacted olefin and the formed aldehyde by decomposition or extraction, and (b) a second step in which the mixture of the unreacted mono-olefin and the formed aldehyde freed from the cobalt catalyst in the first step is reacted with a gas mixture of carbon monoxide and hydrogen with use of a cobalt organophophine complex catalyst at a high temperature under high pressure thereby simultaneously hydroformylating the unreacted mono-olefin and hydrogenating the aldehyde to form the alcohol.

11 Claims, 2 Drawing Figures

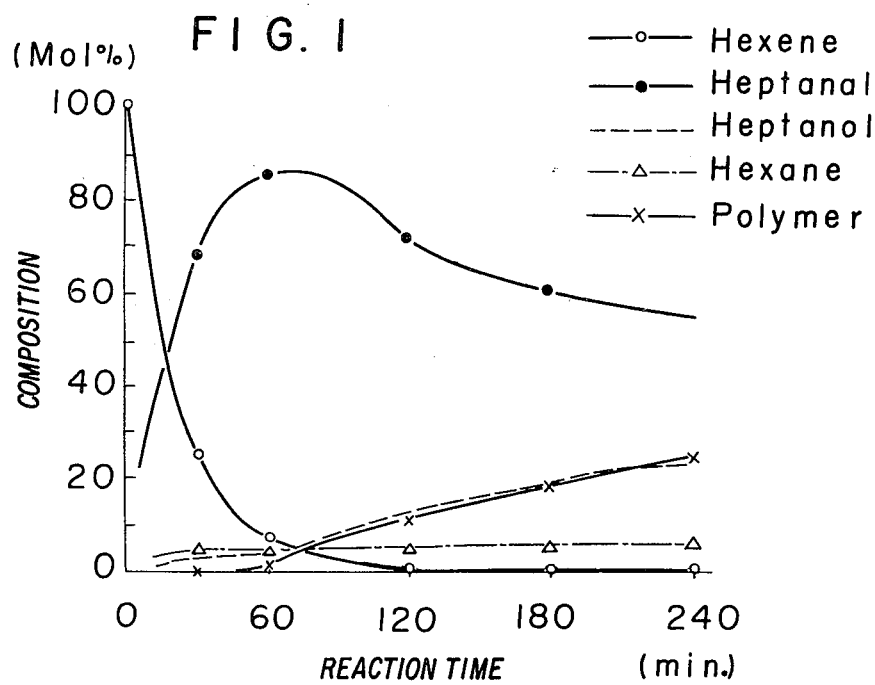
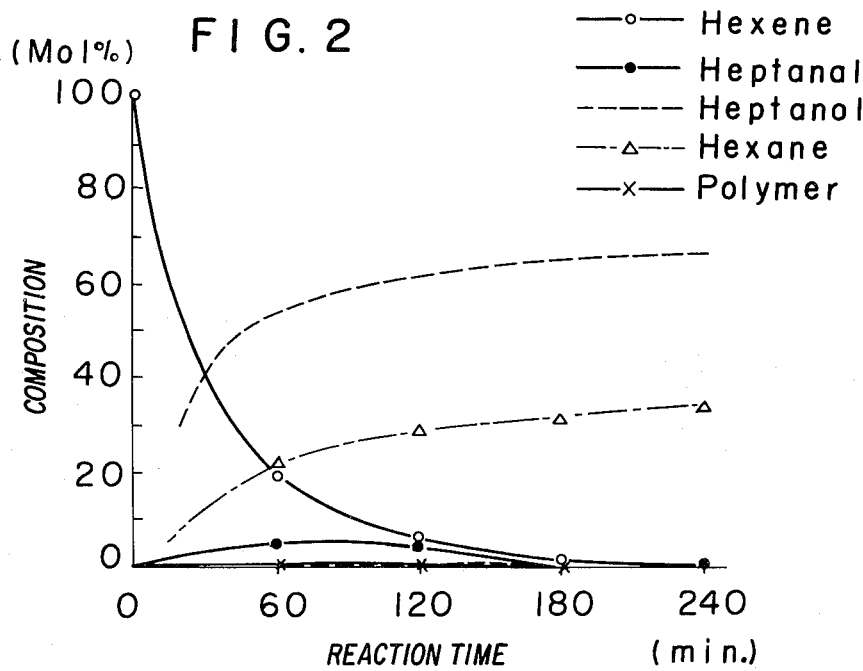

PROCESS FOR PRODUCING AN ALCOHOL BY HYDROFORMYLATION

BACKGROUND OF THE INVENTION

1. Field of the Invention

The present invention relates to a process for producing an alcohol by hydroformylation which comprises reacting a monoolefin with carbon monoxide and hydrogen to form an alcohol having carbon atoms greater in number by one than the carbon atoms of the monoolefin.

2. Description of the Prior Art

For last ten years, so-called oxoalcohols have been used in great amounts for a variety of purposes, for instance, as intermediates for plasticizers for various polymers, as starting materials for synthetic detergents, as intermediates for agricultural chemicals, medicines or fine chemicals such as food additives or as various solvents, and they have been constantly in demand. The manufacturers are competing one another in an effort to supply such oxoalcohols steadily and inexpensively. Under these circumstances, various new catalytic systems have been proposed and various efforts are being made for improvement of the oxo process.

Especially in view of the oil shortage in recent years, it is desired to improve the yield of alcohols from olefin raw materials and to save the energy required for the process.

In the conventional oxo processes, it is common to use a cobalt carbonyl as a catalyst. The cobalt carbonyl catalyst is highly active, whereby the reaction rate of the olefin is quite high and the selectivity of its conversion to the corresponding aldehyde is fairly high. However, the alcohol subsequently formed by hydrogenation of the aldehyde in the presence of the cobalt carbonyl catalyst is likely to react with the aldehyde in the same reaction system to form undesirable products such as acetal. Thus, such a conventional process has a drawback that the formation of the high boiling point products increases as the conversion rate of the olefin is raised. In particular, when the conversion rate of the olefin is raised to a level higher than 95 mol % under the usual industrial reaction conditions, it is almost impossible to suppress the formation of the high boiling point products. Further, the product from the oxo process will have to be hydrogenated, after removal of the cobalt carbonyl catalyst, by same means to obtain the desired alcohol. This hydrogenation is usually carried out by a method in which the product from the oxo process is, after removal of the catalyst, passed through a fixed bed catalyst column under hydrogen pressure at a high temperature. As the fixed bed catalyst, a copper chromite catalyst, or a nickel or cobalt catalyst supported on silica or alumina is usually used. Depending upon its surface conditions, such a catalyst tends to lead to various side reactions to produce high boiling point products. Thus, various difficulties are involved in the selection of the hydrogenation catalyst.

In an attempt to overcome the difficulties, a cobalt organophosphine complex catalyst having a biphilic ligand such as trivalent phosphorus has been developed whereby the hydroformylation of the olefin and the hydrogenation of the formed aldehyde are conducted in a single step, as disclosed in Japanese Examined Patent Publication No. 1402/1964. According to this process, the formation of the high boiling point products can substantially be suppressed and the stability of the catalyst is improved whereby the pressure can be reduced. A further feature of this process is that when a straight chained monoolefin is used as the starting material, the selectivity of the conversion of the formed aldehyde to the straight chained alcohol is quite high as compared with the other conventional processes. However, such a catalyst having a biphilic ligand composed of Co and trivalent phosphorus has an increased hydridic character and therefore naturally tends to lead to direct hydrogenation of the olefin to the corresponding paraffin. Accordingly, even when the optimum conditions are selected and a straight chained terminal olefin is used as the starting material, a considerable amount of the paraffin will be formed as an impurity although it depends upon the structure of the trivalent phosphorus. When a branched olefin or an inner olefin is used, the conversion of the olefin into the paraffin by the direct hydrogenation takes place at a selectivity of at least 20 mol % of the converted olefin.

SUMMARY OF THE INVENTION

It is an object of the present invention to overcome the above mentioned difficulties inherent to the conventional processes and to provide a process whereby an alcohol can be produced in good yield on an industrial scale.

The present invention provides a process for producing an alcohol by hydroformylation which comprises reacting a straight chained, branched or alicyclic monoolefin having from 3 to 20 carbon atoms with carbon monoxide and hydrogen to form an alcohol having carbon atoms greater in number by one than the carbon atoms of the monoolefin, wherein the improvement comprises (a) a first step in which the monoolefin is hydroformylated with use of a cobalt catalyst in the presence of a gas mixture of carbon monoxide and hydrogen at a high temperature under high pressure to selectively form an aldehyde at a conversion of the monoolefin being from 50 to 95 mol % while suppressing the formation of an alcohol, and the cobalt catalyst is then removed from the unreacted olefin and the formed aldehyde by decomposition or extraction, and (b) a second step in which the mixture of the unreacted monoolefin and the formed aldehyde freed from the cobalt catalyst in the first step is reacted with a gas mixture of carbon monoxide and hydrogen with use of a cobalt organophophine complex catalyst at a high temperature under high pressure thereby simultaneously hydroformylating the unreacted monoolefin and hydrogenating the aldehyde to form the alcohol.

BRIEF DESCRIPTION OF THE DRAWINGS

FIG. 1 is a graph illustrating the formation of various products in a conventional oxo process which was conducted under the conditions described in Comparative Example 1 given hereinafter.

FIG. 2 is similar to FIG. 1 but illustrates the results obtained by another conventional process which was conducted under the conditions described in Comparative Example 2 given hereinafter.

DETAILED DESCRIPTION OF THE PREFERRED EMBODIMENTS

As mentioned above and as illustrated in FIG. 1, in the conventional oxo process wherein a cobalt carbonyl catalyst is used, a considerable amount of high boiling point products (which is identified as "polymer" in FIG. 1) is formed as an impurity, and this tendency is pronounced with an increase of the conversion rate of the olefin. Whereas, in the second conventional process wherein the hydroformylation of the olefin and the hydrogenation of the formed aldehyde are conducted in a single step in the presence of a cobalt organophosphine complex catalyst, a paraffin is formed as an impurity by direct hydrogenation of the olefin starting material although the formation of the high boiling product can thereby substantially be suppressed. This is illustrated in FIG. 2.

Whereas, according to the present invention, the oxo process i.e. hydroformylation, is carried out in two steps, whereby the oxo alcohol can be prepared in much better yield than in the conventional processes and yet the energy consumption is substantially reduced.

The monoolefin starting material may be a straight chained, branched or alicyclic monoolefin having from 3 to 20 carbon atoms or a mixture of such monoolefins.

In the first step, the monoolefin is reacted with a gas mixture of carbon monooxide and hydrogen at a high temperature and high pressure in the presence of a cobalt catalyst which preferably is cobalt carbonyl represented by the formula $HCo(CO)_4$ or $Co_2(CO)_8$, under such conditions that the monoolefin is selectively converted into the corresponding aldehyde at a conversion of from 50 to 95 mol % without substantial formation of the alcohol. Namely, the first step is conducted in a manner similar to the conventional process wherein the cobalt carbonyl catalyst is used, but the reaction is controlled so that the conversion of the monoolefin is from 50 to 95 mol %. As mentioned above, if the conversion rate exceeds 95 mol %, it will be extremely difficult to suppress the formation of undesirable high boiling point products. Then, the cobalt catalyst is removed from the reaction mixture comprising the unreacted olefin and the formed aldehyde either by decomposing it or by extracting it. The separated cobalt catalyst may advantageously be reused for the hydroformylation in the first step.

In the second step, the mixture of the unreacted monoolefin and the formed aldehyde from which the cobalt catalyst has been removed in the first step, is reacted with a gas mixture of carbon monoxide and hydrogen in the presence of a cobalt organophosphine complex catalyst, whereby the hydroformylation of the unreacted monoolefin and hydrogenation of the aldehyde take place simultaneously to form the desired alcohol in good yield without leading to side reactions.

Now, a preferred embodiment of the present invention will be described in detail.

In the first step, the cobalt catalyst is added to the olefin starting material in an amount of from 0.05 to 1.00% by weight, preferably from 0.1 to 0.6% by weight, as cobalt metal in the olefin. The cobalt catalyst may be added in any form, for example, in a form of an inorganic or organic salt of Co. However, in a catalyst system for the purpose of the present invention, the catalyst is preferably in a form of $HCo(CO)_4$ or $Co_2(CO)_8$.

The olefin in which cobalt is dissolved, is hydroformylated in the presence of a gas mixture of hydrogen and carbon monoxide in a volume ratio of the hydrogen to the carbon monoxide of from 0.8 to 2.0, preferably from 1.0 to 1.6, under pressure of from 150 to 250 kg/cm$^2$ (gauge pressure) at a temperature of from 80° to 180° C. These reaction conditions and the reaction time are suitably controlled depending upon the structure of the olefin and the position of the double bond in the olefin to bring the conversion of the monoolefin to a level of from 50 to 95 mol %, whereby it is possible to substantially completely suppress the formation of high boiling point products.

Further, a suitable additive may be added to ensure the suppression of the formation of the high boiling point products. For instance, it is effective to add water in an amount of from 2 to 10% by weight, preferably from 3 to 8% by weight, based on the olefin.

From the reaction product thus obtained, the cobalt catalyst is removed by a known method. As a method for removing the cobalt catalyst, it is preferred to treat the reaction mixture with an aqueous sodium hydroxide solution under elevated pressure, whereupon the cobalt carbonyl is transferred to the aqueous phase in a form of its sodium salt, and after the phase separation, the sodium salt in the aqueous phase is acidified and then reused as a catalyst for the first step.

The reaction mixture thus obtained by the hydroformylation of the first step, composed mainly of the aldehyde and freed from cobalt, is, after once depressurizing, used as the raw material for the hydroformylation of the second step. The reaction of the second step is carried out by dissolving Co in the product of the first step in the same manner as in the first step. The Co concentration in this second step is from 0.2 to 2.00% by weight as cobalt metal dissolved in the reaction product of the first step, and phosphorus is further added in a form of a trialkylphosphine to bring the molar ratio of phosphorus/cobalt to a level of from 1.1 to 5.0, preferably from 2.0 to 3.5.

As the trialkylphosphine to be added, there may be mentioned phosphines having an alkyl or cycloalkyl group of at least 4 carbon atoms, such as tri(butyl)phosphine, tri(pentyl)phosphine, tri(hexyl)phosphine, tri(heptyl)phosphine, tri(octyl)phosphine, tri(decyl)phosphine and tri(cyclohexyl)phosphine. These phosphines are readily available.

It is also possible to preliminarily prepare a complex of cobalt carbonyl and phosphorus and then to add the complex quantitatively to the product of the first step.

The reaction product of the first step thus containing the cobalt phosphine complex catalyst is reacted with a gas mixture of hydrogen and carbon monoxide in a volume ratio of the hydrogen to the carbon monoxide of from 1.1 to 10, under pressure of from 30 to 200 kg/cm$^2$ (gauge pressure), preferably from 30 to 100 kg/cm$^2$ (gauge pressure), at a temperature of from 160° to 250° C., preferably from 180° to 210° C. It is desirable to maintain the volume ratio of hydrogen/carbon monoxide in the reaction system within a range of from 1.1 to 10, whereby the formation of high boiling point products can substantially be suppressed. By conducting the reaction under these reaction conditions, it is possible to obtain a product composed of a paraffin and the desired alcohol substantially free from the olefin or aldehyde. The content of the high boiling point products formed by side reactions is minimum. The product thus obtained is subjected to distillation whereby the paraffine is distilled off and further the majority of the alcohol is distilled to obtain the final alcohol. The catalyst solution containing the residual alcohol from the distilled bottom can be reused as the catalyst for the reaction of the second step.

The alcohol obtainable by the above process is a high quality alcohol substantially free from impurities.

Industrially, the present invention is carried out in a continuous process, whereby the yield can further effectively be improved.

Now, the invention will be described with reference to Examples. However, it should be understood that the present invention is not limited to these specific examples.

EXAMPLE 1

Into a 100 ml stainless steel autoclave equipped with a stirrer, 34 g of propylene dimer $C_6$ olefin starting material comprising 92% by weight of 2-methylpentene-1, 5% by weight of hexenes, 2% by weight of 2,3-dimethylbutenes, and 1% by weight of 4-methylpentenes, was charged, and 0.2 g of dicobalt octacarbonyl crystals [$CO_2(CO)_8$] as the catalyst prepared separately by a conventional method were dissolved therein (2 g/kg of the olefins, as cobalt metal). After flushing with nitrogen, a gas mixture of $H_2/CO=1.3$ (volume ratio) was supplied to bring the pressure in the autoclave to 120 kg/cm$^2$G. This autoclave was placed in an electric heater and gradually heated. When the temperature reached about 120° C., the gas absorption started. Then, the gas mixture of $H_2/CO=1.3$ (volume ratio) was continuously supplied through a control valve to maintain the pressure in the autoclave constant at 160 kg/cm$^2$G. Thirty minutes after the temperature reached 140° C., the stirring was stopped, and the reaction mixture was rapidly cooled to room temperature, depressurized and withdrawn from the autoclave. After removal of the catalyst, the product was washed with water and then analyzed by gas chromatography. The quantitative analysis by the gas chromatography was carried out with use of $C_{11}$ normal paraffin as the internal standard, whereby it was found that the product comprises 3.0% by weight of $C_6$ paraffins composed mainly of 2-methylpentane, 15.0% by weight of unreacted olefins, 80.3% by weight of $C_7$ aldehydes, 1.7% by weight of $C_7$ alcohols and no substantial high boiling products.

Into a 100 ml stainless steel autoclave equipped with a stirrer and flushed with nitrogen, 40.0 g of the product from the first step was charged for the reaction of the second step, and 0.5 g of dicobalt octacarbonyl crystals prepared separately by a conventional method were dissolved therein (4.3 g/kg of the olefins, as cobalt metal) and then 2.16 g of a commercially available tri-normal octylphosphine was introduced under nitrogen stream to bring the molar ratio of P/Co to 2. To this autoclave, 70 kg/cm$^2$G of a gas mixture of $H_2/CO=2$ (volume ratio) was supplied and the autoclave was gradually heated. When the temperature reached about 190° C., the gas absorption started, and then reaction was conducted at a temperature of 200° C. while controlling the pressure to be 100 kg/cm$^2$G by means of the control valve. Upon completion of the reaction, the autoclave was gradually cooled, and the reaction product was analyzed by the gas chromatography based on the internal standard method as described above, whereby it was found that the product comprised 5.5% by weight of $C_6$ paraffins, a trace amount of unreacted olefins, 0.2% by weight of $C_7$ aldehydes, 93.6% by weight of $C_7$ alcohols and 0.7% by weight of high boiling products.

COMPARATIVE EXAMPLE 1

Into a 100 ml of stainless steel autoclave equipped with a stirrer, 34 g of the olefin starting material of Example 1 was charged, and 0.2 g of dicobalt octacarbonyl crystals as the catalyst was dissolved therein. After flushing with nitrogen, a gas mixture of $H_2/CO=1.3$ (volume ratio) was supplied to bring the pressure in the autoclave to 120 kg/cm$^2$G. This autoclave was placed in an electric heater and heated, and the reaction was conducted for 3 hours and 15 minutes at a temperature of 150° C. while continuously supplying the gas mixture of $H_2/CO=1.3$ (volume ratio) to maintain the pressure at 160 kg/cm$^2$G. After removal of the catalyst, the reaction product was analyzed by gas chromatography, whereby it was found that the product comprised 3.7% by weight of $C_6$ paraffins, 1.1% by weight of unreacted olefins, 57.8% by weight of $C_7$ aldehydes, 17.9% by weight of $C_7$ alcohols and 19.5% by weight of high boiling products.

To 43 g of this product, 2 g of a commercially available copper-chromite powdery hydrogenation catalyst and 2 g of a commercially available nickel powdery hydrogenation catalyst were added, and the hydrogenation reaction was conducted for 4 hours at a temperature of 170° C. while maintaining the hydrogen pressure at 50 kg/cm$^2$G. After completion of the reaction, the product was separated from the catalyst and then analyzed by the gas chromatography based on the internal standard method, whereby it was found that the product comprised 4.9% by weight of $C_6$ paraffins, 82.8% by weight of $C_7$ alcohols and 12.3% by weight of high boiling products.

COMPARATIVE EXAMPLE 2

Into a 100 ml stainless steel autoclave equipped with a stirrer, 34 g of the olefin starting material of Example 1 was charged, and 0.5 g of dicobalt octacarbonyl crystals as the catalyst were dissolved therein and then 2.16 g of a commercially available trinormal octylphosphine was introduced under nitrogen stream to bring the molar ratio of P/Co to 2.

To this autoclave, 70 kg/cm$^2$G of a gas mixture of $H_2/CO=2$ (volume ratio) was supplied and the autoclave was heated. The reaction was conducted for 4 hours at a temperature of 200° C. while continuously supplying the gas mixture of $H_2/CO=2.0$ (volume ratio) to maintain the pressure at 100 kg/cm$^2$G. After cooling, the reaction product was withdrawn and analyzed by gas chromatography based on the internal standard method, whereby it was found that the product comprised 28.0% by weight of $C_6$ paraffins, 0.4% by weight of unreacted olefins, 0.4% by weight of $C_7$ aldehydes, 71.2% by weight of $C_7$ alcohols and a trace amount of high boiling products.

EXAMPLES 2 TO 5

Into a 100 ml stainless steel autoclave equipped with a stirrer, 50 ml of each of four kinds of olefins was introduced respectively, and the two step hydroformylation was conducted in the same manner as in Example 1 with respect to each of the four kinds of the olefins under the conditions shown in Table 1. The respective final products gave the results as shown in the last part of Table 1.

TABLE 1

|  | Example 2 | Example 3 | Example 4 | Example 5 |
|---|---|---|---|---|
| Reaction conditions: | | | | |
| First step reaction | | | | |
| Olefins used | Isooctene (n-butene dimer) | Isononene (propylene trimer) | $C_{6-9}$ straight chained 1-olefins (wax cracking product) | Cyclohexene |
| Amount of catalyst Co g/kg of olefins (supplied in a form of $Co_2(CO)_8$) | 2.1 | 6 | 1.7 | 3.0 |
| Temperature (°C.) | 150 | 150 | 140 | 140 |
| $H_2/CO$ (volume ratio) | 1.3 | 1.3 | 1.3 | 1.3 |
| Pressure (kg/cm² G) | 160 | 160 | 160 | 160 |
| Reaction time (min.) | 120 | 60 | 40 | 60 |
| Second step reaction | | | | |
| Amount of catalyst (Co) Co g/kg of olefins | 6.0 | 6.0 | 4.0 | 4.0 |
| Trioctylphosphine P/Co (mol/mol) | 2 | 2 | 2 | 2 |
| Temperature (°C.) | 200 | 200 | 200 | 200 |
| $H_2/CO$ volume ratio | 2.0 | 2.0 | 2.0 | 2.0 |
| Pressure (kg/cm² G) | 100 | 100 | 50 | 100 |
| Reaction time (min.) | 180 | 350 | 120 | 180 |
| Second step reaction products | | | | |
| Composition (wt. %) (as measured by gas chromatography) | | | | |
| Hydrocarbon | 7.4 | 17.8 | 5.2 | 12.9 |
| Alcohol | Isononanol 91.9 | Isodecanol 81.9 | $C_{7-10}$ alcohols 93.4 (average straight chained ratio:65.8) | Cyclohexyl-methanol 86.5 |
| Polymers | 0.7 | 0.3 | 1.4 | 0.6 |

EXAMPLES 6 AND 7

The same starting material and apparatus as in Example 2 were used. The reaction conditions are mostly similar to Example 2, but the P/Co ratio and the $H_2/CO$ ratio were changed as shown in Table 2.

TABLE 2

|  | Example 6 | Example 7 |
|---|---|---|
| Reaction conditions: | | |
| First step reaction | | |
| Olefins used | Isooctene (n-butene dimer) | Isooctene (n-butene dimer) |
| Amount of catalyst Co g/kg of olefins (supplied in a form of $Co_2(CO)_8$) | 2.1 | 2.1 |
| Temperature (°C.) | 150 | 150 |
| $H_2/CO$ (volume ratio) | 1.3 | 1.3 |
| Pressure (kg/cm² G) | 160 | 160 |
| Reaction time (min.) | 120 | 120 |
| Second step reaction | | |
| Amount of catalyst (Co) Co g/kg of olefins | 6.0 | 6.0 |
| Trioctylphosphine P/Co (mol/mol) | 1.1 | 2.0 |
| Temperature (°C.) | 200 | 200 |
| $H_2/CO$ (volume ratio) | 2.0 | 1.1 |
| Pressure (kg/cm² G) | 100 | 100 |
| Reaction time (min.) | 180 | 180 |
| Second step reaction Products | | |
| Composition (wt. %) (as measured by gas chromatography) | | |
| Hydrocarbon | 7.0 | 7.2 |
| Alcohol | 92.0 | 92.1 |
| Polymer | 1.0 | 0.7 |

We claim:

1. In a process for producing an alcohol by hydroformylation which comprises reacting straight chained, branched, or alicyclic mono-olefin having from 3 to 20 carbon atoms with carbon monoxide and hydrogen to form an alcohol having carbon atoms greater in number by one than the carbon atoms of the mono-olefin, the improvement which comprises:

(a) a first step in which the mono-olefin is hydroformylated with use of a cobalt carbonyl catalyst selected from the group consisting of $HCo(CO)_4$ and $Co_2(CO)_8$ catalysts in the presence of a gas mixture of carbon monoxide and hydrogen in a volume ratio of the hydrogen to the carbon monoxide of from 0.8 to 2.0 at a temperature of from 80° to 180° C. under pressure of from 150 to 250 kg/cm² to selectively form an aldehyde at a conversion of the mono-olefin being from 50 to 95 mol % while suppressing the formation of an alcohol, and the cobalt carbonyl catalyst is then removed from the unreacted olefin and the formed aldehyde by decomposition or extraction, and (b) a second step in which the mixture of the unreacted mono-olefin and the formed aldehyde freed from the cobalt carbonyl catalyst in the first step is reacted with a gas mixture of carbon monoxide and hydrogen in a volume ratio of the hydrogen to the carbon monoxide of from 1.1 to 10 with use of a cobalt trialkylphosphine complex catalyst at a temperature of from 160° to 250° under pressure of from 30 to 200 kg/cm$^2$ thereby simultaneously hydroformylating the unreacted mono-olefin and hydrogenating the aldehyde to form the alcohol.

2. The process according to claim 1 wherein the reaction in the second step is carried out under pressure of from 30 to 100 kg/cm$^2$ at a temperature of from 180° to 210° C.

3. The process according to claim 1 wherein the cobalt catalyst in the first step is used in an amount of from 0.05 to 1.00% by weight as cobalt metal in the olefin.

4. The process according to claim 3 wherein the cobalt catalyst in the first step is used in the amount of from 0.1 to 0.6% by weight as cobalt metal in the olefin.

5. The process according to claim 1 wherein the volume ratio of the hydrogen to the carbon monoxide is from 1.0 to 1.6.

6. The process according to claim 1 wherein an additive to suppress the formation of high boiling products is added to the reaction system in the first step.

7. The process according to claim 6 wherein water in an amount of from 2 to 10% by weight based on the olefin is added as the additive.

8. The process according to claim 1 wherein the cobalt trialkylphosphine complex catalyst in the second step comprises a cobalt carbonyl in an amount of from 0.2 to 2.00% by weight as cobalt metal based on the product of the first step and a trialkylphosphine in an amount to bring the molar ratio of phosphorus/cobalt to be from 1.1 to 5.0.

9. The process according to claim 8 wherein the molar ratio of phosphorus/cobalt is from 2.0 to 3.5.

10. The process according to claim 8 wherein the trialkylphosphine is selected from tri(butyl)phosphine, tri(pentyl)phosphine, tri(hexyl)phosphine, tri(heptyl)phosphine, tri(octyl)phosphine, tri(decyl)phosphine and tri(cyclohexyl)phosphine.

11. The process according to claim 1 wherein the cobalt catalyst removed from the unreacted olefin and the formed aldehyde in the first step is reused as a catalyst for the first step and after completion of the reaction of the second step, the cobalt trialkylphosphine catalyst is separated from the reaction product and reused as a catalyst for the second step.

* * * * *